United States Patent
Lee et al.

(10) Patent No.: US 11,482,728 B2
(45) Date of Patent: Oct. 25, 2022

(54) NON-AQUEOUS ELECTROLYTE SOLUTION FOR LITHIUM SECONDARY BATTERY AND LITHIUM SECONDARY BATTERY INCLUDING THE SAME

(71) Applicant: LG Chem, Ltd., Seoul (KR)

(72) Inventors: Hyun Yeong Lee, Daejeon (KR); Chul Haeng Lee, Daejeon (KR); Sung Hoon Yu, Daejeon (KR); Hyun Seung Kim, Daejeon (KR)

(73) Assignee: LG Energy Solution, Ltd.

( * ) Notice: Subject to any disclaimer, the term of this patent is extended or adjusted under 35 U.S.C. 154(b) by 337 days.

(21) Appl. No.: 16/610,758

(22) PCT Filed: Nov. 23, 2018

(86) PCT No.: PCT/KR2018/014521
§ 371 (c)(1),
(2) Date: Nov. 4, 2019

(87) PCT Pub. No.: WO2019/107838
PCT Pub. Date: Jun. 6, 2019

(65) Prior Publication Data
US 2020/0075997 A1    Mar. 5, 2020

(30) Foreign Application Priority Data

Nov. 30, 2017 (KR) .................. 10-2017-0163100

(51) Int. Cl.
*H01M 10/0567* (2010.01)
*H01M 4/505* (2010.01)
(Continued)

(52) U.S. Cl.
CPC ....... *H01M 10/0567* (2013.01); *H01M 4/505* (2013.01); *H01M 4/525* (2013.01); *H01M 10/052* (2013.01); *H01M 10/0568* (2013.01)

(58) Field of Classification Search
CPC .................. H01M 10/0567; H01M 10/0568
See application file for complete search history.

(56) References Cited

U.S. PATENT DOCUMENTS

2007/0009806 A1   1/2007   Kim
2007/0171596 A1   7/2007   Chacko et al.
(Continued)

FOREIGN PATENT DOCUMENTS

CN   107069091 A    8/2017
EP   2779277 A1    9/2014
(Continued)

OTHER PUBLICATIONS

Machine translation of JP2000-299127A (Year: 2000).*
(Continued)

*Primary Examiner* — Ryan S Cannon
(74) *Attorney, Agent, or Firm* — Lerner, David, Littenberg, Krumholz & Mentlik, LLP (57) ABSTRACT

A non-aqueous electrolyte solution for a lithium secondary battery, and a lithium second battery including the same are disclosed herein. In some embodiments, the lithium electrolyte includes lithium bis(fluorosulfonyl)imide as a first lithium salt, a second lithium salt, an organic solvent, and a compound represented by Formula 1. In some embodiments, the lithium second battery includes a positive electrode having a positive electrode active material represented by Formula 2.

6 Claims, 3 Drawing Sheets

(51) Int. Cl.
*H01M 4/525* (2010.01)
*H01M 10/052* (2010.01)
*H01M 10/0568* (2010.01)

(56) References Cited

U.S. PATENT DOCUMENTS

| | | | |
|---|---|---|---|
| 2007/0242412 A1 | 10/2007 | Chacko et al. | |
| 2014/0186722 A1* | 7/2014 | Lim | H01M 10/0567 |
| | | | 429/331 |
| 2014/0272532 A1 | 9/2014 | Park et al. | |
| 2014/0272605 A1 | 9/2014 | Lim et al. | |
| 2016/0329600 A1* | 11/2016 | Lee | H01M 4/623 |
| 2020/0028212 A1* | 1/2020 | Hirakawa | H01M 10/0567 |

FOREIGN PATENT DOCUMENTS

| | | |
|---|---|---|
| JP | 2000299127 A | 10/2000 |
| JP | 200152743 A | 2/2001 |
| JP | 2006294414 A | 10/2006 |
| KR | 100709838 B1 | 4/2007 |
| KR | 100833041 B1 | 5/2008 |
| KR | 101190463 B1 | 10/2012 |
| KR | 20160006136 A | 1/2016 |
| KR | 20160036809 A | 4/2016 |
| WO | 2012132957 A1 | 10/2012 |

OTHER PUBLICATIONS

Extended European Search Report including Written Opinion for Application No. EP18883224.0 dated Apr. 7, 2020, 7 pages.
Li et al., "In-situ Neutron Diffraction Study of a High Voltage Li (Ni0.42Mn0.42Co0.16)O2/Graphite Pouch Cell", Electrochimica Acta, Accepted Aug. 22, 2015, vol. 180, pp. 234-240.
International Search Report from Application No. PCT/KR2018/014521 dated Feb. 27, 2019, 2 pages.
Search Report for Chinese Application No. 201880029091.8 dated Nov. 12, 2021. 3 pgs.

\* cited by examiner

NON-AQUEOUS ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2018/014521, filed on Nov. 23, 2018, which claims priority from Korean Patent Application No. 10-2017-0163100, filed on Nov. 30, 2017, the disclosures of which are incorporated by reference herein.

TECHNICAL FIELD

The present invention relates to a non-aqueous electrolyte solution for a lithium secondary battery and a lithium secondary battery including the same.

BACKGROUND ART

In line with miniaturization, lightweight, thin profile, and portable trends in electronic devices according to the development of information and telecommunications industry, the need for high energy density lithium secondary batteries used as power sources of such electronic devices has increased.

Lithium secondary batteries, specifically, lithium ion batteries (LIB), as batteries that may best meet the need, have been adopted as power sources of many portable devices due to high energy density and ease of design.

Recently, a lithium secondary battery, which may maintain excellent performance not only at room temperature but also in a more severe outside environment such as a high-temperature or low-temperature environment, is required as the range of the lithium secondary batteries used has expanded from conventional small electronic devices to large electronic devices, cars, or smart grids.

A lithium secondary battery currently used is composed of a carbon-based negative electrode capable of intercalating and deintercalating lithium ions, a positive electrode formed of a lithium-containing transition metal oxide, and a non-aqueous electrolyte solution in which an appropriate amount of a lithium salt is dissolved in a carbonate-based non-aqueous organic solvent, wherein charge and discharge may be possible while a phenomenon is repeated in which lithium ions, which are deintercalated from the positive electrode by charging, are intercalated into the carbon-based negative electrode and again deintercalated during discharging.

With respect to the lithium secondary battery, a kind of a passivation layer is formed on a surface of the negative electrode while some of electrolyte solution additive components and organic solvents are decomposed in a voltage range of 0.5 V to 3.5 V during initial charge and the negative electrode reacts with the electrolyte solution. The layer is denoted as a "solid electrolyte interface (SEI) layer".

The SEI layer formed during the initial charge may not only act as an ion tunnel to only pass lithium ions, but may also prevent a reaction of the lithium ions with the carbon-based negative electrode or other materials during charge and discharge. That is, the ion tunnel prevents the destruction of a structure of the carbon-based negative electrode due to the co-intercalation of the carbon-based negative electrode and the organic solvents of the electrolyte solution having a high molecular weight which solvate lithium ions and moves therewith.

Therefore, in order to improve high-temperature cycle characteristics and low-temperature output of the lithium secondary battery, there is a need to develop a technique for forming a robust SEI layer on the surface of the negative electrode of the lithium secondary battery.

In a case in which the organic solvent used in the non-aqueous electrolyte solution of the lithium secondary battery is generally stored for a long period of time at high temperature, gas is generated while the organic solvent is oxidized by the transition metal oxide discharged from the positive electrode, and battery swelling and electrode assembly deformation occur due to the gas thus generated. Also, the negative electrode is exposed while the SEI layer is gradually collapsed during high-temperature storage in a fully charged state (e.g., storage at 60° C. after charged to a state of charge (SOC) of 100% at 4.2 V). Since the exposed negative electrode reacts with the electrolyte solution to continuously cause a side reaction, gases, such as CO, $CO_2$, $CH_4$, and $C_2H_6$, are generated, and, as a result, an internal pressure of the battery is increased to cause battery deformation such as battery swelling. If an internal short circuit of the battery is caused by the battery deformation, fire or explosion of the battery may occur while the battery is deteriorated.

In order to address this limitation, a method of adding an SEI forming material for preventing the collapse of the SEI in the non-aqueous electrolyte solution has been suggested. However, another limitation may occur in which cycle life characteristics of the secondary battery are degraded as other side effects are caused by the electrolyte solution additive.

Thus, there is a continuous need to develop a non-aqueous electrolyte solution with a new configuration which may improve overall performance of the lithium secondary battery while minimizing the side effects.

PRIOR ART DOCUMENT

Japanese Patent Application Laid-open Publication WO2012-132957

DISCLOSURE OF THE INVENTION

Technical Problem

An aspect of the present invention provides a non-aqueous electrolyte solution for a lithium secondary battery which includes an additive capable of forming a robust ion conductive film on the surface of a negative electrode during initial charge of the secondary battery.

Another aspect of the present invention provides a lithium secondary battery in which cycle life characteristics are improved by including the non-aqueous electrolyte solution for a lithium secondary battery.

Technical Solution

According to an aspect of the present invention, there is provided a non-aqueous electrolyte solution for a secondary battery including:
lithium bis(fluorosulfonyl)imide (hereinafter, referred to as "LiFSI") as a first lithium salt;
a second lithium salt,
an organic solvent, and a compound represented by Formula 1 below:
[Formula 1]

First, the second lithium salt is a lithium salt excluding LiFSI as the first lithium salt, wherein the second lithium salt may include Li$^+$ as a cation, and may include at least one selected from the group consisting of F$^-$, Cl$^-$, Br$^-$, I$^-$, NO$_3^-$, N(CN)$_2^-$, ClO$_4^-$, BF$_4^-$, B$_{10}$C$_{10}^-$, PF$_6^-$, CF$_3$SO$_3^-$, CH$_3$CO$_2^-$, CF$_3$CO$_2^-$, AsF$_6^-$, SbF$_6^-$, AlCl$_4^-$, AlO$_4^-$, CH$_3$SO$_3^-$, BF$_2$C$_2$O$_4^-$, BC$_4$O$_8^-$, PF$_4$C$_2$O$_4^-$, PF$_2$C$_4$O$_8^-$, (CF$_3$)$_2$PF$_4^-$, (CF$_3$)$_3$PF$_3^-$, (CF$_3$)$_4$PF$_2^-$, (CF$_3$)$_5$PF$^-$, C$_4$F$_9$SO$_3^-$, CF$_3$CF$_2$SO$_3^-$, (CF$_3$SO$_2$)$_2$N$^-$, (FSO$_2$)$_2$N$^-$, CF$_3$CF$_2$(CF$_3$)$_2$CO$^-$, (CF$_3$SO$_2$)$_2$CH$^-$, (SF$_5$)$_3$C$^-$, (CF$_3$SO$_2$)$_3$C$^-$, CF$_3$(CF$_2$)$_7$SO$_3^-$, SCN$^-$, and (CF$_3$CF$_2$SO$_2$)$_2$N$^-$ as an anion.

A molar ratio of the first lithium salt to the second lithium salt may be in a range of 1:1 to 1:2, for example, 1:1.2 to 1:1.4.

Also, the compound represented by Formula 1 may be included in an amount of 0.1 wt % to 1 wt %, for example, 0.2 wt % to 0.7 wt % based on a total weight of the non-aqueous electrolyte solution.

According to another aspect of the present invention, there is provided a lithium secondary battery including a positive electrode, a negative electrode, a separator, and a non-aqueous electrolyte solution, wherein the positive electrode includes a lithium transition metal oxide represented by Formula 2 as a positive electrode active material, and the non-aqueous electrolyte solution is the non-aqueous electrolyte solution for a secondary battery of the present invention.

Li(Ni$_a$Co$_b$Mn$_c$)O$_2$  [Formula 2]

In Formula 2,
$0.55<a\leq0.9$, $0.05\leq b<0.3$, $0.05\leq c<0.3$, and $a+b+c=1$.

The positive electrode active material may include at least one selected from the group consisting of Li(Ni$_{0.6}$Mn$_{0.2}$Co$_{0.2}$)O$_2$, Li(Ni$_{0.7}$Mn$_{0.15}$Co$_{0.15}$)O$_2$, and Li(Ni$_{0.8}$Mn$_{0.1}$Co$_{0.1}$)O$_2$.

Advantageous Effects

According to the present invention, a lithium secondary battery having improved initial capacity and cycle life characteristics may be prepared by including a non-aqueous electrolyte solution for a lithium secondary battery, which include an additive capable of forming a robust ion conductive film on a negative electrode during initial charge of the secondary battery, and a positive electrode which includes a transition metal oxide containing a large amount of nickel (Ni) as a positive electrode active material.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Specifically, in an embodiment of the present invention, provided is a non-aqueous electrolyte solution for a secondary battery including:

lithium bis(fluorosulfonyl)imide as a first lithium salt,
a second lithium salt,
an organic solvent, and
a compound represented by Formula 1 below:

[Formula 1]

(1) First Lithium Salt

The non-aqueous electrolyte solution of the present invention includes lithium bis(fluorosulfonyl)imide (LiFSI), which may form a robust and thin solid electrolyte interface (SEI) on a surface of an electrode, as a first lithium salt.

As a result, since the non-aqueous electrolyte solution may suppress a side reaction of the electrolyte solution with the electrode, for example, may suppress decomposition of a surface of a positive electrode and may prevent an oxidation reaction of the electrolyte solution, the non-aqueous electrolyte solution may improve output characteristics. Particularly, since the SEI derived from the lithium bis(fluorosulfonyl)imide is thin, the movement of lithium ions in a negative electrode may be more facilitated, and thus, the output characteristics of the secondary battery may be more improved.

(2) Second Lithium Salt

Also, in the non-aqueous electrolyte solution of the present invention, the second lithium salt is a lithium salt excluding LiFSI as the first lithium salt, wherein it is not particularly limited, and, for example, the second lithium salt may include Li$^+$ as a cation, and may include at least one selected from the group consisting of $F^-$, $Cl^-$, $Br^-$, $I^-$, $NO_3^-$, $N(CN)_2^-$, $ClO_4^-$, $BF_4^-$, $B_{10}Cl_{10}^-$, $PF_6^-$, $CF_3SO_3^-$, $CH_3CO_2^-$, $CF_3CO_2^-$, $AsF_6^-$, $SbF_6^-$, $AlCl_4^-$, $AlO_4^-$, $CH_3SO_3^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $C_4F_9SO_3^-$, $CF_3CF_2SO_3^-$, $(CF_3SO_2)_2N^-$, $FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $SCN^-$, and $(CF_3CF_2SO_2)_2N^-$ as an anion.

Specifically, the lithium salt may include a single material selected from the group consisting of LiCl, LiBr, LiI, LiClO$_4$, LiBF$_4$, LiB$_{10}$Cl$_{10}$, LiPF$_6$, LiCF$_3$SO$_3$, LiCH$_3$CO$_2$, LiCF$_3$CO$_2$, LiAsF$_6$, LiSbF$_6$, LiAlCl$_4$, LiAlO$_4$, LiCH$_3$SO$_3$, lithium fluorosulfonyl imide (LiFSI, LiN(SO$_2$F)$_2$), lithium (bis)trifluoromethanesulfonimide (LiTFSI, LiN(SO$_2$CF$_3$)$_2$), and lithium bisperfluoroethanesulfonimide (LiBETI, LiN(SO$_2$C$_2$F$_5$)$_2$), or a mixture of two or more thereof.

Specifically, the lithium salt may include a single material selected from the group consisting of LiPF$_6$, LiBF$_4$, LiCH$_3$CO$_2$, LiCF$_3$CO$_2$, LiCH$_3$SO$_3$, LiFSI, LiTFSI, and LiN(C$_2$F$_5$SO$_2$)$_2$, or a mixture of two or more thereof. However, the lithium salt does not include LiDFP which is a lithium salt included in the additive.

The first lithium salt and the second lithium salt may be included in a normally usable concentration range, and may specifically be included in a concentration of 0.3 M to 3 M, for example, 0.5 M to 1.2 M in the electrolyte solution. In a case in which the concentration of the lithium salt is greater than 3 M, a lithium ion-transfer effect may be reduced due to an increase in viscosity of the non-aqueous electrolyte solution, and it is difficult to form a uniform SEI due to a decrease in wettability of the non-aqueous electrolyte solution.

The first lithium salt and the second lithium salt may be included in a molar ratio of 1:1 to 1:2, for example, 1:1.2 to 1:1.4.

In a case in which the molar ratio of the first lithium salt to the second lithium salt is within the above range, occurrence of a swelling phenomenon due to the excessive occurrence of side reactions in the electrolyte solution during charge and discharge of the battery may be prevented, and a reduction in output of the secondary battery may be prevent. Specifically, if the molar ratio of the first lithium salt is less than 1 or the molar ratio of the second lithium salt is greater than 2, a number of irreversible reactions may occur during the formation of the SEI on the surface of the negative electrode or during the intercalation of lithium ions solvated by a carbonate-based solvent into the negative electrode, and an effect of improving cycle and capacity characteristics as well as low-temperature output of the secondary battery may be insignificant due to exfoliation of the surface of the negative electrode (e.g., carbon surface layer) and decomposition of the electrolyte solution. Also, if the molar ratio of the first lithium salt is greater than 1 or the molar ratio of the second lithium salt is less than 1, since the excessive amount of the first lithium salt is included to cause corrosion of an electrode assembly during charge and discharge, stability of the secondary battery may be reduced.

(3) Organic Solvent

In the present invention, a type of the organic solvent is not limited as long as the organic solvent may minimize decomposition due to an oxidation reaction during charge and discharge of the secondary battery and may exhibit desired characteristics with the additive. For example, a carbonate-based solvent, an ether-based solvent, an ester-based solvent, or an amide-based solvent may be used alone or in a mixture of two or more thereof.

The carbonate-based solvent among the organic solvents may include at least one solvent selected from the group consisting of a cyclic carbonate-based solvent and a linear carbonate-based solvent.

Specific examples of the cyclic carbonate-based solvent may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof, and the cyclic carbonate-based solvent may more specifically include any one selected from the group consisting of ethylene carbonate, propylene carbonate, 1,2-butylene carbonate, 2,3-butylene carbonate, vinylene carbonate, and fluoroethylene carbonate (FEC), or a mixture of two or more thereof.

Specific examples of the linear carbonate-based solvent may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, and the linear carbonate-based solvent may more specifically include any one selected from the group consisting of dimethyl carbonate, diethyl carbonate, dipropyl carbonate, and ethylmethyl carbonate, or a mixture of two or more thereof.

Also, as the ether-based solvent, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

Furthermore, the ester-based solvent may include at least one compound selected from the group consisting of a linear ester-based solvent and a cyclic ester-based solvent.

Specific examples of the linear ester-based solvent may be any one selected from the group consisting of methyl acetate, ethyl acetate, propyl acetate, methyl propionate, ethyl propionate, propyl propionate, and butyl propionate, or a mixture of two or more thereof, but the present invention is not limited thereto.

Specific examples of the cyclic ester-based solvent may be any one selected from the group consisting of γ-butyrolactone, γ-valerolactone, γ-caprolactone, σ-valerolactone, and ε-caprolactone, or a mixture of two or more thereof, but the present invention is not limited thereto.

It is known that the cyclic carbonate-based solvent well dissociates the lithium salt in the electrolyte due to high permittivity as a highly viscous organic solvent. Particularly, a non-aqueous electrolyte solution having high electrical conductivity may be prepared when the above cyclic carbonate-based solvent is mixed with the low viscosity, low permittivity linear carbonate-based solvent, such as dimethyl carbonate and diethyl carbonate, and the linear ester-based compound in an appropriate ratio and used.

The cyclic carbonate-based solvent and the linear carbonate-based solvent may be mixed and used as the organic solvent used in the non-aqueous electrolyte solution of the present invention, and a weight ratio of the cyclic carbonate-based solvent:the linear carbonate-based solvent may be in a range of 10:90 to 70:30.

(4) Additive

As described above, the non-aqueous electrolyte solution for a lithium secondary battery of the present invention may include the compound represented by the following Formula 1 as an additive:

[Formula 1]

In general, an SEI affecting a battery reaction is formed on a surface of a negative electrode (graphite) while an electrolyte solution is decomposed before lithium ions discharged from a positive electrode are intercalated into the negative electrode during initial charge of a secondary battery. The SEI not only has the property of passing the lithium ions and blocking movement of electrons, but also acts as a protective film that prevents the electrolyte solution from being decomposed continuously. Thus, when the robust SEI is formed on the surface of the negative electrode, the decomposition of the electrolyte solution due to the movement of the electrons between the electrode and the electrolyte solution is suppressed and only the intercalation and deintercalation of the lithium ions selectively becomes possible. However, it is difficult to continuously maintain performance of the formed SEI, and the formed SEI may be destroyed by shrinkage and expansion due to repeated charge and discharge cycles or by heat or impact from the outside.

Charge is additionally or irreversibly consumed while the destroyed SEI is again formed during the continuous charge and discharge process so that reversible capacity is continuously reduced. Particularly, since interfacial resistance is increased as a thickness of the solid film formed due to the decomposition of the electrolyte solution is increased, battery performance is degraded.

Thus, in the present invention, a lithium secondary battery having improved initial capacity and cycle life characteristics may be prepared by including an additive capable of forming a robust ion conductive film on the surface of the negative electrode in the non-aqueous electrolyte solution.

That is, since the compound of Formula 1 included as the electrolyte additive in the present invention has a molecular structure in which phthalates are substituted with two allyl groups which are double bonds, the compound of Formula 1 may form an allyl radical which is kinetically favorable to other double bond functional groups during electrochemical reduction. Since the allyl radical has a resonance structure, it may form a stable intermediate, and thus, a more stable SEI may be formed on the surface of the electrode. As a result, since the SEI may be robustly well-maintained without being collapsed even if the number of movements of lithium ions increases during high-temperature charge and discharge, charge and discharge capacity and cycle life characteristics of the lithium secondary battery may be effectively maintained.

The compound represented by Formula 1 may be included in an amount of 0.1 wt % to 1 wt %, particularly 0.2 wt % to 0.7 wt %, and more particularly 0.4 wt % to 0.7 wt % based on a total weight of the non-aqueous electrolyte solution.

In a case in which the compound represented by Formula 1 is included in an amount within the above range, a secondary battery having more improved overall performance may be prepared. For example, when the amount of the additive is 0.1 wt % or more, a stabilization effect of the SEI or metal dissolution suppression effect may be improved, and, when the amount of the compound represented by Formula 1 is 1 wt % or less, an effect of forming an SEI may be improved within the range of increase in resistance which may be accommodated. In a case in which the amount of the compound represented by Formula 1 is greater than 1 wt %, since an excessively thick film is formed, resistance may be increased and, accordingly, initial capacity and cycle life characteristics may be degraded.

(5) Additive for Forming SEI

The non-aqueous electrolyte solution according to the embodiment of the present invention may further include an additional additive which may be used with the additives to form a stable film on the surfaces of the negative electrode and the positive electrode while not significantly increasing initial resistance in addition to the effect from the additives, or which may act as a complementary agent for suppressing the decomposition of the solvent in the non-aqueous electrolyte solution and improving the mobility of lithium ions.

The additional additive is not particularly limited as long as it is an additive for forming an SEI which may form a stable film on the surfaces of the positive electrode and the negative electrode.

Specifically, as a representative example, the additive for forming an SEI may include at least one additive for forming an SEI which is selected from the group consisting of a halogen-substituted carbonate-based compound, a nitrile-based compound, a cyclic carbonate-based compound, a phosphate-based compound, a borate-based compound, and a lithium salt-based compound.

Specifically, the halogen-substituted carbonate-based compound may include fluoroethylene carbonate (FEC) and may be included in an amount of 5 wt % or less based on the total weight of the non-aqueous electrolyte solution. In a case in which the amount of the halogen-substituted carbonate-based compound is greater than 5 wt %, cell swelling performance may deteriorate.

Also, the nitrile-based compound may include at least one compound selected from the group consisting of succinonitrile, adiponitrile (Adn), acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

In a case in which the nitrile-based compound is used with the above-described additives, an effect, such as an improvement of high-temperature characteristics, may be expected due to positive electrode/negative electrode film stabilization. That is, the nitrile-based compound may act as a complementary agent for forming the negative electrode SEI, may play a role in suppressing the decomposition of the solvent in the electrolyte, and may play a role in improving the mobility of the lithium ions. The nitrile-based compound may be included in an amount of 8 wt % or less based on the total weight of the non-aqueous electrolyte solution. In a case in which the total amount of the nitrile-based compound in the non-aqueous electrolyte solution is greater than 8 wt %, since the resistance is increased due to an increase in the film formed on the surface of the electrode, battery performance may deteriorate.

The carbonate-based compound may improve durability of the battery by forming a stable SEI mainly on the surface of the negative electrode during battery activation. The cyclic carbonate-based compound may include vinylene carbonate (VC) or vinyl ethylene carbonate, and may be included in an amount of 3 wt % or less based on the total weight of the non-aqueous electrolyte solution. In a case in which the amount of the cyclic carbonate-based compound in the non-aqueous electrolyte solution is greater than 3 wt %, cell swelling inhibition performance and initial resistance may deteriorate.

Furthermore, since the phosphate-based compound stabilizes $PF_6$ anions in the electrolyte solution and assists in the formation of the positive electrode and negative electrode films, the phosphate-based compound may improve the durability of the battery. The phosphate-based compound may include at least one compound selected from the group consisting of lithium difluoro bis(oxalato)phosphate (LiDFOP), lithium difluorophosphate (LiDFP, $LiPO_2F_2$), lithium tetrafluoro(oxalato)phosphate (LiTFOP), trimethylsilyl phosphite (TMSPi), tris(2,2,2-trifluoroethyl)phosphate (TFEPa), and tris(trifluoroethyl)phosphite (TFEPi), and the phosphate-based compound may be included in an amount of 3 wt % or less based on the total weight of the non-aqueous electrolyte solution.

Since the borate-based compound promotes ion-pair separation of a lithium salt, the borate-based compound may improve the mobility of lithium ions, may reduce the interfacial resistance of the SEI, and may dissociate a material, such as LiF, which may be formed during the battery reaction but is not well separated, and thus, a problem, such as generation of hydrofluoric acid gas, may be solved. The borate-based compound may include lithium bis(oxalato)borate (LiBOB, $LiB(C_2O_4)_2$), lithium oxalyldifluoroborate, or tris(trimethylsilyl)borate (TMSB), and the borate-based compound may be included in an amount of 3 wt % or less based on the total weight of the non-aqueous electrolyte solution.

Also, the lithium salt-based compound is a compound different from the lithium salt included in the non-aqueous electrolyte solution, wherein the lithium salt-based compound may include at least one compound selected from the group consisting of LiODFB and $LiBF_4$ and may be included in an amount of 3 wt % or less based on the total weight of the non-aqueous electrolyte solution.

Two or more additives for forming an SEI may be mixed and used, and the additive for forming an SEI may be included in an amount of 10 wt % or less, and particularly 0.01 wt % to 10 wt %, for example, 0.1 wt % to 5.0 wt % based on a total amount of the electrolyte solution.

In a case in which the amount of the additive for forming an SEI is less than 0.01 wt %, the high-temperature storage characteristics and the gas generation reducing effect to be achieved from the additive may be insignificant, and, in a case in which the amount of the additive for forming an SEI is greater than 10 wt %, the side reaction in the electrolyte solution during charge and discharge of the battery may excessively occur. Particularly, if the excessive amount of the additive for forming an SEI is added, the additive for forming an SEI may not be sufficiently decomposed so that it may be present in the form of an unreacted material or precipitates in the electrolyte solution at room temperature. Accordingly, resistance may be increased to degrade life characteristics of the secondary battery.

Lithium Secondary Battery

Also, in an embodiment of the present invention, there is provided a lithium secondary battery including a positive electrode, a negative electrode, a separator, and a non-aqueous electrolyte solution, wherein the positive electrode includes a lithium transition metal oxide represented by the following Formula 2 as a positive electrode active material, and the non-aqueous electrolyte solution is the non-aqueous electrolyte solution for a lithium secondary battery of the present invention.

$$Li(Ni_aCo_bMn_c)O_2 \quad \text{[Formula 2]}$$

(in Formula 2,
0.55<a≤0.9, 0.05≤b<0.3, 0.05≤c<0.3, and a+b+c=1.)

Specifically, the lithium secondary battery of the present invention may be prepared by injecting the non-aqueous electrolyte solution of the present invention into an electrode assembly composed of a positive electrode, a negative electrode, and a separator disposed between the positive electrode and the negative electrode. In this case, those typically used in the preparation of the lithium secondary battery may all be used as the positive electrode, the negative electrode, and the separator which constitute the electrode assembly.

In this case, the positive electrode, the negative electrode, and the separator, which constitute the lithium secondary battery of the preset invention, may be prepared by a typical method and used.

(1) Positive Electrode

First, the positive electrode may be prepared by forming a positive electrode material mixture layer on a positive electrode collector. The positive electrode material mixture layer may be formed by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may include the lithium transition metal oxide represented by Formula 2 in which an amount of nickel is greater than 0.55, as a representative example, at least one selected from the group consisting of $Li(Ni_{0.6}Mn_{0.2}Co_{0.2})O_2$, $Li(Ni_{0.7}Mn_{0.15}Co_{0.15})O_2$, and $Li(Ni_{0.8}Mn_{0.1}Co_{0.1})O_2$).

Also, the positive electrode active material may further include a lithium composite metal oxide including lithium and at least one metal of cobalt, manganese, nickel, and aluminum, in addition to the lithium transition metal oxide represented by Formula 2.

Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where 0<Y<1), $LiMn_{2-Z}Ni_ZO_4$ (where 0<Z<2), etc.), lithium-nickel-cobalt-based oxide (e.g., $LiNi_{1-Y1}Co_{Y1}O_2$ (where 0<Y1<1), lithium-manganese-cobalt-based oxide (e.g., $LiCo_{1-Y2}Mn_{Y2}O_2$ (where 0<Y2<1), $LiMn_{2-Z1}Co_{Z1}O_4$ (where 0<Z1<2), etc.), lithium-nickel-manganese-cobalt-based oxide (e.g., $Li(Ni_{p1}Co_{q1}Mn_{r2})O_4$ (where 0<p1<2, 0<q1<2, 0<r2<2, and p1+q1+r2=2), etc.), or lithium-nickel-cobalt-transition metal (M) oxide (e.g., $Li(Ni_{p2}Co_{q2}Mn_{r3}M_{S2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), etc.), and any one thereof or a compound of two or more thereof may be included.

The positive electrode active material may be included in an amount of 80 wt % to 99.5 wt %, for example, 85 wt % to 95 wt %, based on a total weight of solid content in the positive electrode slurry. In a case in which the amount of the positive electrode active material is 80 wt % or less, since energy density is reduced, capacity may be reduced.

Also, the binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

Furthermore, any conductive agent may be used as the conductive agent without particular limitation so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

In this case, the conductive agent may have an average particle diameter ($D_{50}$) of 10 μm or less, particularly 0.01 μm to 10 μm, and more particularly 0.01 μm to 1 μm.

The conductive agent is commonly added in an amount of 1 wt % to 30 wt % based on the total weight of the solid content in the positive electrode slurry.

Also, the solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 10 wt % to 60 wt %, for example, 20 wt % to 55 wt %.

(2) Negative Electrode

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metal or an alloy of lithium and the metal, a metal composite oxide, a material which may be doped and undoped with lithium, and a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metal or the alloy of lithium and the metal, a metal selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn), or an alloy of lithium and the metal may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \leq x \leq 1$), $Li_xWO_2$ ($0 \leq x \leq 1$), and $Sn_xMe_{1-x}Me'_yO_z$ (Me: manganese (Mn), Fe, Pb, or Ge; Me': Al, boron (B), phosphorus (P), Si, Groups I, II and III elements of the periodic table, or halogen; $0<x\leq 1$; $1\leq y\leq 3$; $1\leq z\leq 8$) may be used as the metal composite oxide.

The material, which may be doped and undoped with lithium, may include Si, $SiO_x$ ($0<x\leq 2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), rutherfordium (Rf), V, niobium (Nb), Ta, dubidium (Db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and the same conductive agent as that included in the positive electrode active material may be used. For example, a conductive material, such as: graphite such as natural graphite or artificial graphite; carbon black such as acetylene black, Ketjen black, channel black, furnace black, lamp black, and thermal black; conductive fibers such as carbon fibers and metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as selectively the binder and the conductive agent are included. For example, the solvent may be included in an amount such that a concentration of the solid content in the negative electrode slurry including the negative electrode active material as well as selectively the binder and the conductive agent is in a range of 50 wt % to 85 wt %, for example, 50 wt % to 75 wt %.

(3) Separator

Also, the separator plays a role in blocking an internal short circuit between both electrodes and impregnating the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but the lithium secondary battery may have various shapes, such as a cylindrical shape, a prismatic shape, a pouch shape, or a coin shape, depending on purposes. The lithium secondary battery according to the embodiment of the present invention may be a pouch type secondary battery.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-Aqueous Electrolyte Solution Preparation)

A non-aqueous electrolyte solution of the present invention was prepared by adding 0.4 g of the compound represented by Formula 1, as an additive, to 99.6 g of a non-aqueous organic solvent (ethylene carbonate (EC): ethylmethyl carbonate (EMC)=volume ratio of 20:80) in which 0.5M of LiFSI and 0.7M of $LiPF_6$ were dissolved.

(Secondary Battery Preparation)

$Li(Ni_{0.8}Mn_{0.1}Co_{0.1})O_2$ as positive electrode active material particles, carbon black as a conductive agent, and polyvinylidene fluoride (PVDF), as a binder, were added to N-methyl-2-pyrrolidone (NMP), as a solvent, in a weight ratio of 98:1:1 to prepare a positive electrode active material slurry (solid content 55 wt %). A 20 μm thick positive electrode collector (Al thin film) was coated with the positive electrode active material slurry, dried, and roll-pressed to prepare a positive electrode.

Next, a negative electrode active material (artificial graphite/natural graphite=weight ratio of 90:10), carbon black as a conductive agent, a styrene-butadiene rubber (SBR) as a binder, and CMC, as a thickener, were added to NMP, as a solvent, in a weight ratio of 95.6:1:2.3:1.1 to prepare a negative electrode active material slurry (solid content 85 wt %). A 10 μm thick negative electrode collector (Cu thin film) was coated with the negative electrode active material slurry, dried, and roll-pressed to prepare a negative electrode.

After an electrode assembly was prepared by a typical method of sequentially stacking a polyethylene porous film with the above-prepared positive electrode and negative electrode, the electrode assembly was accommodated in a case, 400 μl of the above-prepared non-aqueous electrolyte solution was injected, and, after the case was vacuum sealed at −85 kPa, a wetting process was performed for one day at room temperature to prepare a lithium secondary battery of the present invention.

Examples 2

A non-aqueous electrolyte solution and a lithium secondary battery including the same were prepared in the same manner as in Example 1 except that 0.2 g of the compound represented by Formula 1 and 0.2 g of vinylene carbonate were mixed and added as an additive during the preparation of the non-aqueous electrolyte solution.

Example 3

A non-aqueous electrolyte solution and a lithium secondary battery including the same were prepared in the same manner as in Example 1 except that 0.7 g of the compound represented by Formula 1 was included in 99.3 g of the non-aqueous organic solvent during the preparation of the non-aqueous electrolyte solution.

Example 4

A non-aqueous electrolyte solution and a lithium secondary battery including the same were prepared in the same manner as in Example 1 except that 0.05 g of the compound represented by Formula 1 was included in 99.95 g of the non-aqueous organic solvent during the preparation of the non-aqueous electrolyte solution.

Example 5

A non-aqueous electrolyte solution and a lithium secondary battery including the same were prepared in the same manner as in Example 1 except that 1.3 g of the compound represented by Formula 1 was included in 98.7 g of the non-aqueous organic solvent during the preparation of the non-aqueous electrolyte solution.

Comparative Example 1

A non-aqueous electrolyte solution and a lithium secondary battery including the same were prepared in the same manner as in Example 1 except that 0.4 g of vinylene carbonate was added instead of the compound represented by Formula 1 during the preparation of the non-aqueous electrolyte solution.

TABLE 1

|  | Lithium salt (M) | | | Non-aqueous organic solvent | | Additive (amount g) | |
|---|---|---|---|---|---|---|---|
|  | LiFSI | LiPF$_6$ | Molar ratio of LiFSI:LiPF$_6$ | Type (volume ration) | Addition amount (g) | VC | Formula 1 |
| Example 1 | 0.5 | 0.7 | 1:1.4 | EC:EMC = 20:80 | 99.6 | — | 0.4 |
| Example 2 | 0.5 | 0.7 | 1:1.4 | EC:EMC = 20:80 | 99.6 | 0.2 | 0.2 |
| Example 3 | 0.5 | 0.7 | 1:1.4 | EC:EMC = 20:80 | 99.3 | — | 0.7 |
| Example 4 | 0.5 | 0.7 | 1:1.4 | EC:EMC = 20:80 | 99.95 | — | 0.05 |
| Example 5 | 0.5 | 0.7 | 1:1.4 | EC:EMC = 20:80 | 98.7 | — | 1.3 |
| Comparative Example 1 | 0.5 | 0.7 | 1:1.4 | EC:EMC = 20:80 | 99.6 | 0.4 | — |

EXPERIMENTAL EXAMPLES

Experimental Example 1

Figure 1:
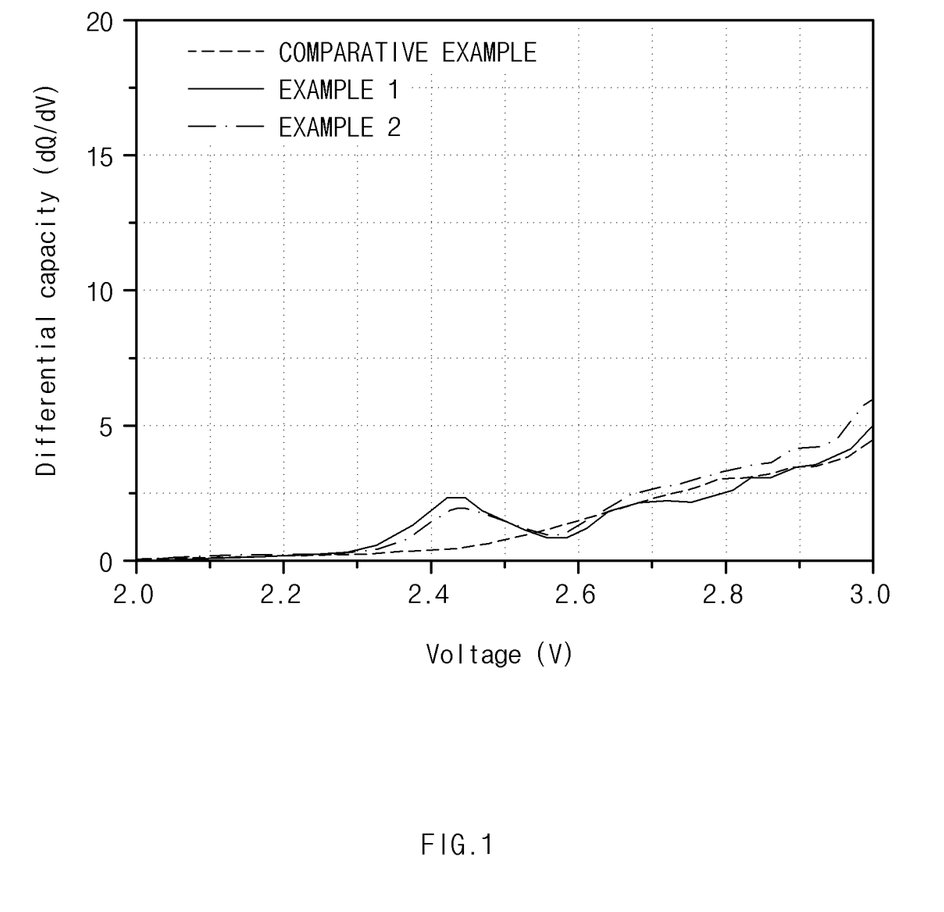
FIG. 1 is a graph illustrating differential capacity curves of lithium secondary batteries according to Experimental Example 1 of the present invention.

After each of the lithium secondary batteries prepared in Examples 1 and 2 and the lithium secondary battery prepared in Comparative Example 1 was charged (subjected to formation) at a constant current of 0.1 C for 3 hours, differential capacity was measured and presented in FIG. 1.

Referring to FIG. 1, with respect to the lithium secondary battery of Comparative Example 1, a peak did not appear up to 2.8 V, but, with respect to the lithium secondary batteries prepared according to Examples 1 and 2, it may be understood that peaks appeared in a range of 2.4 V to 2.5 V.

From these results, it may be indirectly confirmed that, since the compound of Formula 1 included in the non-aqueous electrolyte solution of the present invention was decomposed earlier than the vinylene carbonate included as a non-aqueous electrolyte solution additive, a robust SEI may be formed on the surface of the negative electrode during initial charge.

Experimental Example 2

Each of the secondary batteries prepared in Examples 1 to 5 and the secondary battery prepared in Comparative Example 1 was charged at 0.33 C/4.2 V under a constant current/constant voltage (CC/CV) condition at room temperature (25° C.) until the current reached 1/20 (mA) of a current of 1 C, and then discharged again at a current of 0.33 C to 3 V. Subsequently, initial capacity was measured using PNE-0506 charge/discharge equipment (manufacturer: PNE SOLUTION Co., Ltd., 5 V, 6 A), and the results thereof are presented in Table 2 below.

TABLE 2

|  | Initial capacity (mAh) |
|---|---|
| Example 1 | 56.4 |
| Example 2 | 56.6 |
| Example 3 | 56.4 |
| Example 4 | 56.3 |
| Example 5 | 56.0 |
| Comparative Example 1 | 56.3 |

As illustrated in Table 2, initial capacity of the secondary battery of Comparative Example 1 including the non-aqueous electrolyte solution without the compound of Formula 1 was 56.3 mAh, but initial capacities of the secondary batteries of Examples 1 to 3 were 56.4 mAh, 56.6 mAh, and 56.4 mAh, respectively, wherein it may be understood that the initial capacities were improved in comparison to that of Comparative Example 1.

It may be understood that initial capacity of the secondary battery of Example 4, which included the non-aqueous electrolyte solution including a small amount of the compound of Formula 1, was 56.3 mAh which was similar to that of Comparative Example 1.

Also, with respect to the secondary battery of Example 5 which included the non-aqueous electrolyte solution including an excessive amount of the compound of Formula 1, since resistance was increased, it may be understood that initial capacity was reduced to 56.0 mAh, which was lower than that of the secondary battery of Comparative Example 1.

Experimental Example 3

Each of the secondary batteries prepared in Examples 1 and 2 and the secondary battery prepared in Comparative Example 1 was charged at a constant current (CC) of 0.33 C to a voltage of 4.2 V at room temperature (25° C.), and, thereafter, was charged at a constant voltage (CV) of 4.2 V until the charge current reached 1/20 (mA) of a current of 0.33 C. Thereafter, after each battery was left standing for 10 minutes, each battery was discharged at a constant current (CC) of 0.33 C to a voltage of 3.0 V.

Subsequently, each battery was charged at a constant current (CC) of 0.33 C to a SOC of 50%, and electrochemical impedance spectroscopy (EIS) was then performed.

That is, AC impedance of the battery was measured using a VMP3 potentiostat by Bio-logic Science Instruments while being scanned from 50 mHz to 200 kHz. In this case, amplitude of alternating current applied was 14 mV, and a current response was measured. The results thereof are presented in FIG. 2 below.

Figure 2:
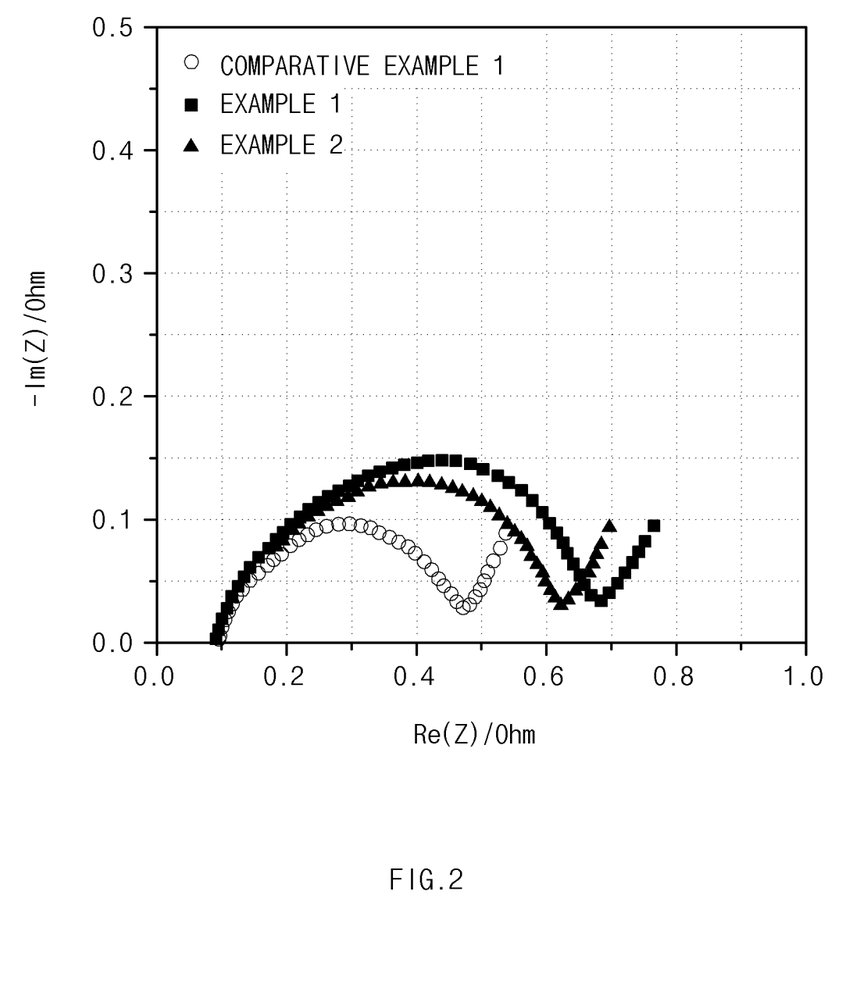
FIG. 2 is a graph illustrating the results of evaluation of AC impendences of lithium secondary batteries according to Experimental Example 3 of the present invention.

Referring to FIG. 2, it may be understood that resistances (impedances) of the secondary batteries of Examples 1 and 2, which included the non-aqueous electrolyte solution including the compound represented by Formula 1, were increased in comparison to that of the secondary battery of Comparative Example 1 which included the non-aqueous electrolyte solution only including vinylene carbonate, as an additive, without the compound represented by Formula 1. Particularly, it may be understood that the resistance of the secondary battery of Example 1, which included the non-aqueous electrolyte solution including a larger amount of the compound represented by Formula 1, was slightly more increased than that of the secondary battery of Example 2. From these results, with respect to the secondary batteries of Examples 1 and 2 which included the non-aqueous electrolyte solution including the compound represented by Formula 1 of the present invention, since a robust SEI was formed on the surface of the negative electrode, it may be understood that the resistance was increased.

Experimental Example 4

Each of the secondary batteries prepared in Examples 1, 2, 4 and 5 and the secondary battery prepared in Comparative Example 1 was charged at 1 C/4.2 V under a constant current/constant voltage (CC/CV) condition at 45° C. until the current reached 1/20 (mA) of a current of 1 C and then discharged again at a current of 1 C to 3 V, and discharge capacity was measured using the PNE-0506 charge/discharge equipment (manufacturer: PNE SOLUTION Co., Ltd., 5 V, 6 A).

The above charging and discharging were set as one cycle, and discharge capacity was measured using the PNE-0506 charge/discharge equipment (manufacturer: PNE SOLUTION Co., Ltd., 5 V, 6 A) while 250 cycles of charging and discharging were repeatedly performed.

Capacity retention was measured by substituting the discharge capacities into the following Equation (1), and the results thereof are presented in FIG. 3 below.

(after $N$ cycles) capacity retention (%)=(discharge capacity after $N$ cycles/discharge capacity after one cycle)×100(%)   Equation (1)

Figure 3:
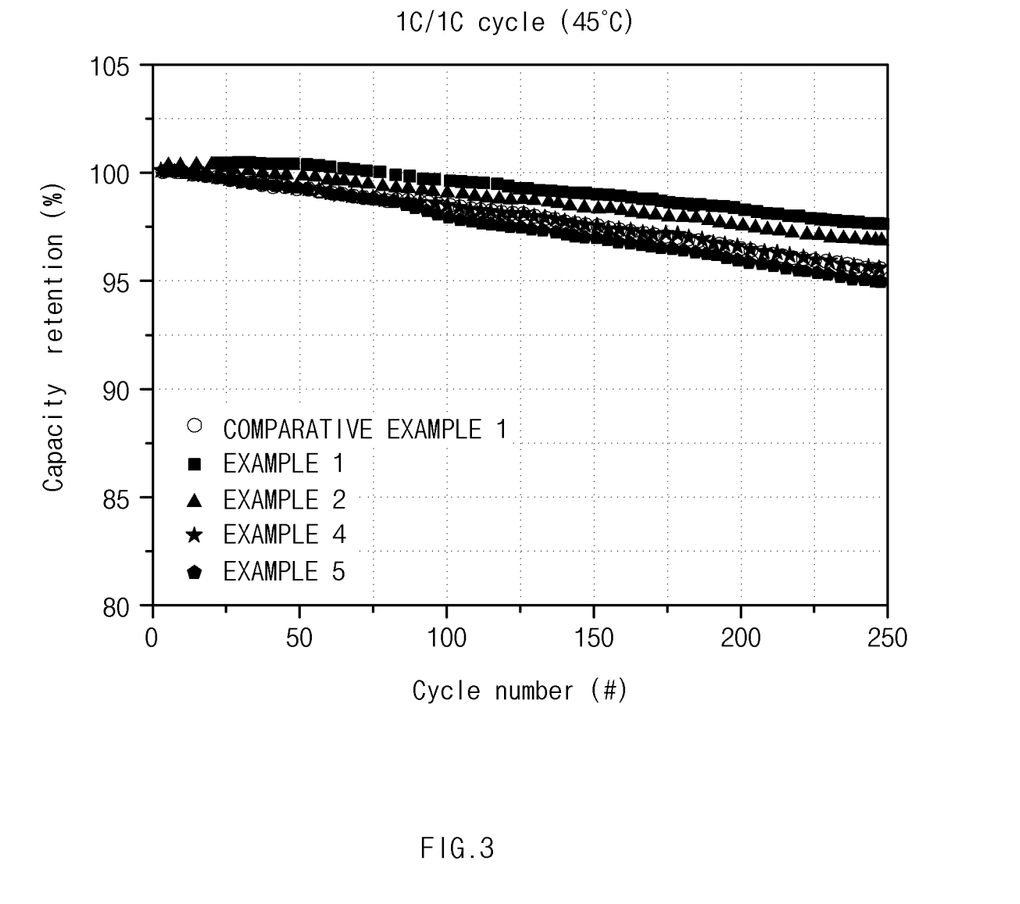
FIG. 3 is a graph illustrating the results of evaluation of capacity retentions of lithium secondary batteries according to Experimental Example 4 of the present invention.

Referring to FIG. 3, it may be understood that capacity retentions after 250 cycles of the secondary batteries of Examples 1 and 2, which included the non-aqueous electrolyte solution including the compound represented by Formula 1 as an additive, were improved in comparison to that of the secondary battery of Comparative Example 1 which included the non-aqueous electrolyte solution not including the compound represented by Formula 1 as an additive.

With respect to the lithium secondary battery of Example 4 which included the non-aqueous electrolyte solution including the small amount of the compound represented by Formula 1 as an additive, since the effect of forming the SEI due to the additive was insignificant, it may be understood that capacity retention was similar to that of Comparative Example 1 as the number of cycles was increased.

Also, with respect to the lithium secondary battery of Example 5 which included the non-aqueous electrolyte solution including the excessive amount of the compound represented by Formula 1, since a side reaction was caused by the additive in the electrolyte solution, it may be understood that capacity retention was reduced in comparison to that of Comparative Example 1 as the number of cycles was increased.

The invention claimed is:

1. A lithium secondary battery, comprising:
a positive electrode;
a negative electrode;
a separator, and
a non-aqueous electrolyte solution;
wherein the positive electrode having a positive electrode active material,
wherein the positive electrode active material comprises a lithium transition metal oxide represented by Formula 2, and
wherein the non-aqueous electrolyte solution comprises:
lithium bis(fluorosulfonyl)imide as a first lithium salt;
a second lithium salt;
an organic solvent;
a compound represented by the following Formula 1,
wherein a molar ratio of the first lithium salt to the second lithium salt is in a range of 1:1.2 to 1:1.4, and
wherein the compound represented by Formula 1 is included in an amount of 0.1 wt % to 1 wt % based on a total weight of the non-aqueous electrolyte solution:

[Formula 1]

[Formula 2]

wherein, in Formula 2, 0.7≤$a$≤0.9, 0.05≤$b$<0.3, 0.05≤$c$<0.3, and $a+b+c=1$.

2. The a lithium secondary battery of claim 1, wherein the second lithium salt comprises a cation and an anion, the cation being Li$^+$, and the anion comprises at least one selected from the group consisting of F$^-$, Cl$^-$, Br$^-$, I$^-$, NO$_3^-$, N(CN)$_2^-$, BF$_4^-$, ClO$_4^-$, AlO$_4^-$, AlCl$_4^-$, PF$_6^-$, SbF$_6^-$, AsF$_6^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $CF_3CF_2(CF_3)_2CO^-$, $(CF_3SO_2)_2CH^-$, $CF_3(CF_2)_7SO_3^-$, $CF_3CO_2^-$, $CH_3CO_2^-$, $SCN^-$, and $(CF_3CF_2SO_2)_2N^-$.

3. The lithium secondary battery of claim 1, wherein the compound represented by Formula 1 is included in an amount of 0.2 wt % to 0.7 wt % based on the total weight of the non-aqueous electrolyte solution.

4. The lithium secondary battery of claim 1, further comprising at least one additive for forming a solid electrolyte interface (SEI) selected from the group consisting of a halogen-substituted carbonate-based compound, a nitrile-based compound, a cyclic carbonate-based compound, a phosphate-based compound, a borate-based compound, and a lithium salt-based compound.

5. The lithium secondary battery of claim 1, wherein the positive electrode active material comprises at least one selected from the group consisting of $Li(Ni_{0.7}Mn_{0.15}Co_{0.15})O_2$ and $Li(Ni_{0.8}Mn_{0.1}Co_{0.1})O_2$.

6. The lithium secondary battery of claim 1, wherein the positive electrode active material is $Li(Ni_{0.8}Mn_{0.1}Co_{0.1})O_2$.

\* \* \* \* \*